United States Patent
Jacob et al.

(10) Patent No.: US 7,018,629 B2
(45) Date of Patent: Mar. 28, 2006

(54) PROBIOTIC COMPOSITIONS FOR THE TREATMENT OF INFLAMMATORY BOWEL DISEASE

(75) Inventors: Harold Jacob, Cedarhurst, NY (US); Samuel Adler, Lawrence, NY (US)

(73) Assignee: The Bio Balance Corporation, New York, NY (US)

( * ) Notice: Subject to any disclaimer, the term of this patent is extended or adjusted under 35 U.S.C. 154(b) by 0 days.

(21) Appl. No.: 10/347,877

(22) Filed: Jan. 22, 2003

(65) Prior Publication Data

US 2004/0067223 A1 Apr. 8, 2004

(30) Foreign Application Priority Data

Oct. 6, 2002 (IL) ................................................ 152127

(51) Int. Cl.
*A01N 63/00* (2006.01)
*C12N 1/20* (2006.01)
*C12N 1/00* (2006.01)

(52) U.S. Cl. .................. 424/93.48; 435/849; 435/252.8

(58) Field of Classification Search ................ 435/849, 435/252.8; 424/93.48
See application file for complete search history.

(56) References Cited

U.S. PATENT DOCUMENTS

| | | | |
|---|---|---|---|
| 5,110,795 A | 5/1992 | Hahn | |
| 5,112,856 A | 5/1992 | Gaginella et al. | |
| 5,216,002 A | 6/1993 | Gidda et al. | |
| 5,238,931 A | 8/1993 | Yoshikawa et al. | |
| 5,292,771 A | 3/1994 | Backstrom et al. | |
| 5,312,818 A | 5/1994 | Rubin et al. | |
| 5,324,738 A | 6/1994 | Dinan et al. | |
| 5,331,013 A | 7/1994 | Ahlman et al. | |
| 5,340,801 A | 8/1994 | Ewing et al. | |
| 5,368,854 A | 11/1994 | Rennick | |
| 5,391,555 A | 2/1995 | Marshall et al. | |
| 5,552,439 A | 9/1996 | Panetta | |
| 5,569,680 A | 10/1996 | Wu | |
| 5,599,795 A | 2/1997 | McCann et al. | |
| 5,604,231 A | 2/1997 | Smith et al. | |
| 5,691,343 A | 11/1997 | Sandborn | |
| 5,693,645 A | 12/1997 | Sharpe et al. | |
| 6,297,015 B1 | 10/2001 | Shafran | |
| 6,348,452 B1 | 2/2002 | Brown et al. | |
| 6,500,423 B1 * | 12/2002 | Olshenitsky et al. | 424/93.3 |
| 6,645,530 B1 * | 11/2003 | Borody | 424/543 |
| 2002/0006432 A1 | 1/2002 | Collins et al. | |

FOREIGN PATENT DOCUMENTS

| | | |
|---|---|---|
| WO | WO 95/16461 | 6/1995 |
| WO | WO 97/35596 | 10/1997 |
| WO | WO 02/43649 | 6/2002 |

OTHER PUBLICATIONS

Faubion et al. "Probiotic Theraphy with *E.coli* for Ulcerative Colitis: Take the Good with the Bad". Gastroenterology. 2000; 118:630–631.*
Northfield tc, "Ulcerative Colitis and Crohn's Colitis: Differential Diagnosis and Treatment", Drugs, 14: 198–206, 1977.
Blaker et al., "Immunopathology of Ulcerative Colitis and Crohn's Disease, Nonsurgical Therapeutic Considerations", Eur. J. Pediatr., 139: 162–164, 1982.
Singleton JW, "Inflamatory Bowel Disease", The Gastroenterology Annual: 268–310, 1983.
Saco et al., "Pseudomembranous (antibiotic–associated) Colitis", J. Amer. Acad. Dermatol., 4: 619–629, 1981.
Prantera et al. "Clinical and Laboratory Parameters in Crohn's disease : relation to disease activity, morphology, and extent". Ital. J. Gastroenterol., 13: 24–27, 1981.
Sales et al, "The Prognosis of Inflammatoey Bowel Disease", Arch. Int. Med., 143: 294–299, 1983.

* cited by examiner

*Primary Examiner*—Vera Afremova
(74) *Attorney, Agent, or Firm*—G. E. Ehrlich (1995) Ltd.

(57) ABSTRACT

Pharmaceutical compositions of probiotic *E. coli* strains and uses thereof for treating inflammatory bowel disease.

15 Claims, 4 Drawing Sheets

(4 of 4 Drawing Sheet(s) Filed in Color)

Pre Probactrix

Post Probactrix

Pre ProBactrix

Post Pro Bactrix

PROBIOTIC COMPOSITIONS FOR THE TREATMENT OF INFLAMMATORY BOWEL DISEASE

FIELD AND BACKGROUND OF THE INVENTION

The present invention relates to methods and pharmaceutical compositions for treating and/or preventing inflammatory bowel disease (IBD) and, more particularly, to the use of probiotics for treating and/or preventing IBD, such as Crohn's disease and IBD-related symptoms such as abdominal pain and cramping, diarrhea, rectal and/or intestinal bleeding, weight loss and fever.

Inflammatory bowel disease, or IBD, is a collective term encompassing related, but distinct, chronic inflammatory disorders of the gastrointestinal tract, such as Crohn's disease, ulcerative colitis (UC), indeterminate colitis, microscopic colitis and collagenous colitis, with Crohn's disease and ulcerative colitis being the most common diseases. Ulcerative colitis is confined to the large intestine (colon) and rectum, and involves only the inner lining of the intestinal wall. Crohn's disease may affect any section of the gastrointestinal tract (e.g., mouth, esophagus, stomach, small intestine, large intestine, rectum and anus) and may involve all layers of the intestinal wall. Both diseases, as well as other IBD, are characterized by abdominal pain and cramping, diarrhea, rectal and/or intestinal bleeding, weight loss and fever. The symptoms of these diseases are usually progressive, and sufferers typically experience periods of remission followed by severe flare-ups. Less frequent, but also possible, IBD symptoms reflect mucosal inflammation of other sections of the GI tract, such as duodenitis, jejunitis and proctitis.

A detailed description of IBD symptoms is found in, for example, Northfield, Drugs, Vol. 14, pages 198–206 (1977); Blaker et al, Eur. J. Pediatr., Vol. 139, pages 162–164 (1982); Singleton, The Gastroenterology Annual, pages 268–310 (1983); Saco et al, J. Amer. Acad. Dermatol., Vol. 4, pages 619–629 (1981); Prantera et al, Ital. J. Gastroenterol., Vol. 13, pages 24–27 (1981); Sales et al, Arch. Int. Med., Vol. 143, pages 294–299 (1983); and Ament, Inflammatory Bowel Diseases, Martinus Nijhoff Publ., Boston, Mass., pages 254–268 (1982).

For most patients, IBD is a chronic condition with symptoms lasting for months to years. It is most common in young adults, but can occur at any age. It is found worldwide, but it is most common in industrialized countries such as the United States, England, and northern Europe. In fact, IBD affects an estimated two million people in the United States alone. Although IBD is not considered a fatal illness, prolonged disease can lead to severe malnutrition affecting growth or to the formation of abscesses or intestinal scar tissue, leading in turn to infection or bowel obstruction. Protracted IBD is also known as a risk factor for colon cancer.

Diagnosis of IBD is based on the clinical symptoms, the use of a barium enema, and/or direct visualization (sigmoidoscopy or colonoscopy), with the latter being the most accurate test. For the diagnosis of Crohn's disease, see U.S. Pat. Nos. 6,348,452 and 6,297,015.

The exact causes of IBD are not yet understood. Common hypotheses include, for example, disorders in the immune system and actions of pro-inflammatory cytolines and selective activation of lymphocyte subsets, which perpetuate unrestrained activation of an inflammatory response in the intestine.

IBD has no cure. Patients afflicted with IBD are generally treated currently with therapies that are directed at reducing the inflammatory processes, and at reducing the effects of the inflammatory processes on the patients. The presently known medical treatment of IBD is intended to decrease the number, frequency and severity of acute exacerbations of inflammatory bowel disease and to preventing secondary complications, but at best, the results are disappointing.

The presently known methods for treating IBD have involved anti-inflammatory drugs, immunosuppressive drugs and surgery.

The most commonly used medications to treat IBD are anti-inflammatory drugs such as the salicylates. Preparations of salicylate are effective in treating mild to moderate disease and can also decrease the frequency of disease flares when the medications are taken on a prolonged basis. Examples of salicylates include sulfasalazine, olsalazine, and mesalamine. Particularly, sulfasalazine and related drugs having the bioactive 5-amino-salicylic acid (5-ASA) moiety are widely used to control moderate IBD symptoms and to maintain remission. All of these medications are given orally in high doses for maximal therapeutic benefit. However, treatments with these medications is typically accompanied with adverse side effects such as nausea, dizziness, changes in blood chemistry (including anemia and leukopenia), skin rashes and drug dependence.

Corticosteroids are more potent and faster-acting anti-inflammatory drugs in the treatment of IBD, as compared with salicylates. Prednisone, for example, is a corticosteroid commonly used in the treatment of severe cases of IBD. Nevertheless, potentially serious side effects limit the use of corticosteroids to patients with more severe disease. Side effects of corticosteroids usually occur upon long term use and include thinning of the bone and skin, infections, diabetes, muscle wasting, rounding of faces, psychiatric disturbances, and, on rare occasions, destruction of hip joints.

In cases where IBD patients do not respond to salicylates or corticosteroids, medications that suppress the immune system, namely immunosupprpressants, are used. Examples of immunosuppressants include azathioprine and 6-mercaptopurine. However, as immunosuppressants may render the patient immuno-compromised and susceptible to other diseases, the use thereof in the treatment of IBD is not recommended.

In more severe cases or when the drug therapy fails to relieve the symptoms of IBD, surgical procedures are used. Typical surgical procedures include colectomy, proctocolectomy and ileostomy (See, Cecil Textbook of Medicine, 19th Edition, Wyngaarden et al, ed., 1992). These surgical treatments are radical procedures that often profoundly alter the everyday life of the patient.

In addition to the presently common methods of treating IBD described above, other methods of treating gastrointestinal disorders are disclosed in U.S. Pat. No. 5,110,795 (Hahn), U.S. Pat. No. 5,112,856 (Gaginella et al), U.S. Pat. No. 5,216,002 (Gidda et al), U.S. Pat. No. 5,238,931 (Yoshikawa et al), U.S. Pat. No. 5,292,771 (Backstrom et al), U.S. Pat. No. 5,312,818 (Rubin et al), U.S. Pat. No. 5,324,738 (Dinan et al), U.S. Pat. No. 5,331,013 (Ahlman et al), U.S. Pat. No. 5,340,801 (Ewing et al), U.S. Pat. No. 5,368,854 (Rennick), U.S. Pat. No. 5,391,555 (Marshall et al), U.S. Pat. No. 5,552,439 (Panetta), U.S. Pat. No. 5,569,680 (Wu), U.S. Pat. No. 5,599,795 (McCann et al), U.S. Pat. No. 5,604,231 (Smith et al), U.S. Pat. No. 5,691,343 (Sandborn) and U.S. Pat. No. 5,693,645 (Sharpe et al).

The presently known methods for treating IBD fail to provide a solution for IBD sufferers as these methods (i) fail to provide a substantial cure for IBD, but rather provide treatment of the symptoms; and (ii) include either drug therapy that is accompanied by severe adverse side effects or invasive surgical treatments, both affecting the sufferer's quality of life.

There is thus a widely recognized need for new methods of treating IBD, that would include therapies that are safe, effective, side effect-free and non-invasive.

The present inventors have addressed this issue by providing methods and compositions for treating IBD, which are not based on treating the symptoms but rather address one of the basic causes for IBD, namely, the bacterial equilibrium (balance) in the gastrointestinal (GI) tract. More specifically, the present inventors have envisioned that treating IBD using probiotic formulations would result in alteration of the bacterial balance in the GI tract and would thereby substantially ameliorate or cure IBD.

Probiotics are a class of microorganisms defined as live microbial organisms that beneficially affect the animal and human hosts. The beneficial effects include improvement of the microbial balance of the intestinal microflora or improving the properties of the indigenous microflora. The beneficial effects of probiotics may be mediated by a direct antagonistic effect against specific groups of organisms, resulting in a decrease in numbers, by an effect on their metabolism or by stimulation of immunity. Probiotics may suppress viable counts of an undesired organism by producing antibacterial compounds, by competing for nutrients or for adhesion sites. Further, they may alter microbial metabolism by increasing or decreasing enzyme activity or they may stimulate the immune system by increasing antibody levels or increasing macrophage activity.

It is well known in the art that under conditions where the balance of the GI microflora is adversely affected, probiotics become of potential value in restoring the GI microflora and enabling the individual host to return to normal. Treatments of various GI disorders using probiotic compositions are disclosed, for example, in WO95/16461 and in WO 97/35596.

U.S. Patent Application Publication No. 20020006432 to Collins et al. teach a strain of Bifidobacterium isolated from resected and washed human gastrointestinal tract which is said to be significantly immunomodulatory following oral consumption in humans. The strain is taught to be useful in the prophylaxis and/or treatment of undesirable inflammatory activity, especially gastrointestinal inflammatory activity such as inflammatory bowel disease or irritable bowel syndrome.

Recently, it was uncovered that a single species of a non-pathogenic probiotic microorganism derived from *E. coli* is, alone, capable of restoring normal GI flora of man and of a variety of mammals and avians. The beneficial physiological and therapeutic activity of this species in the GI tract is described in detail in U.S. patent application Ser. No. 09/725,846 and in PCT/IL01/01088, which are incorporated by reference as if fully set forth herein. These references teach that the *Escherichia coli* strain BU-230-98 ATCC Deposit No. 202226 (DSM 12799), which is an isolate of the commercially available probiotic *E. coli* M-17 strain, is highly effective in preventing or treating gastro-enteric infections or disorders, maintaining or reinstating normal gastro-intestinal microflora, preventing or treating diarrhea, preventing or treating gastro-enteric infection caused by an enteric pathogen, such as a Gram negative bacterium or Gram positive bacterium, preventing or treating gastro-enteric *Salmonella* infection, preventing or treating infectious diarrhea, caused by, for example *C. difficile, Salmonella*, particularly *S. Shigella, Campylobacter, E. coli, Proteus, Pseudomonas* or *Clostridium* or diarrhea resulting from antibiotic therapy, radiotherapy or chemotherapy, and/or for normalizing the physiological activity of the gastrointestinal tract.

SUMMARY OF THE INVENTION

In experiments conducted in order to further determine the activity of this *E. coli* strain, it was unexpectedly found that strain BU-230-98 ATCC Deposit No. 202226 (DSM 12799), while altering the microbial balance in the GI tract, is highly efficacious agent for treating IBD, such as Crohn's disease and the symptoms associated therewith and for treating other idiopathic inflammation of the small and proximal intestine. Treating IBD with a probiotic microorganism is highly beneficial as it is devoid of the limitations associated with the accepted methods of treating IBD.

Hence, according to one aspect of the present invention there is provided a method of treating an inflammatory bowel disease (IBD) in a subject in need thereof. The method comprising administering to the subject a therapeutically effective amount of a probiotic *Escherichia coli* strain. The probiotic *Escherichia coli* strain is preferably administered to the subject in a liquid formulation and, further preferably, it is administered orally. The therapeutically effective amount preferably ranges between about $10^7$ and about $10^{12}$ viable bacteria per administration, ranging from 1 to 10, preferably about 2–4 administrations per day.

According to another aspect of the present invention there is provided a pharmaceutical composition comprising, as an active ingredient, a probiotic *Escherichia coli* strain. The pharmaceutical composition is packaged in a packaging material and is identified in print on or in the packaging material for use in the treatment or prevention of an inflammatory bowel disease. Preferably, the pharmaceutical composition is a liquid formulation.

According to further features in preferred embodiments of the invention described below, the inflammatory bowel disease is selected from the group consisting of Crohn's disease, ulcerative colitis, indeterminate colitis, microscopic colitis, collagenous colitis, idiopathic inflammation of the small intestine and IBD-related diarrhea.

According to still further features in the described preferred embodiments the probiotic *Escherichia coli* strain is BU-230-98, ATCC Deposit No. 202226 (DSM 12799). Alternatively, the probiotic *Escherichia coli* strain is M-17, from which *Escherichia coli* strain is BU-230-98, ATCC Deposit No. 202226 (DSM 12799) was isolated. *Escherichia coli* strain BU-230-98, ATCC Deposit No. 202226 (DSM 12799) is advantageous over M-17, as it better survives refrigerated storage in a liquid formulation and is at least as efficacious as M-17 and better.

According to still further features in the described preferred embodiments the liquid formulation comprises between about $10^7$ and about $10^{10}$ CFU per ml of the probiotic *Escherichia coli* strain.

According to still further features in the described preferred embodiments the liquid formulation comprises one or more flavoring agent(s) such as Base Strawberry.

According to still further features in the described preferred embodiments the liquid formulation comprises one or more volatile fraction(s) of a plant extract. The volatile fraction is prepared by water extraction of plant material followed by steam distillation of the plant extract under a pressure lower than atmospheric pressure and at a temperature not exceeding 38° C.

According to still further features in the described preferred embodiments the liquid formulation of the present invention further comprises a beehive product, such as propolis.

The present invention successfully addresses the shortcomings of the presently known configurations by providing a method and a pharmaceutical composition for treating inflammatory bowel disease (IBD) with a probiotic *E. coli* strain. Such probiotic treatment is highly advantageous as is compared with the present methods of treating IBD, as it is efficacious, safe, non-invasive and side effect-free.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawings executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
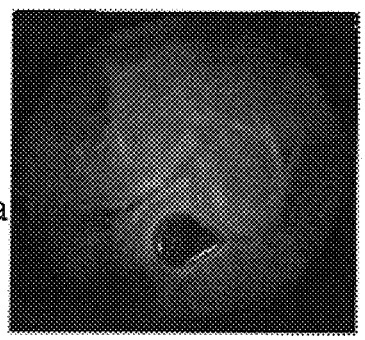
Figure 1C:
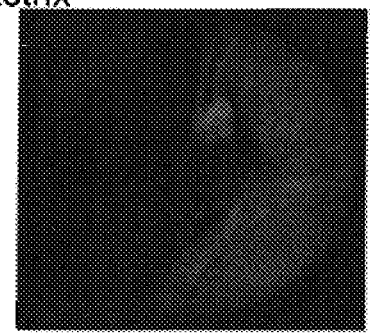
Figure 1B:
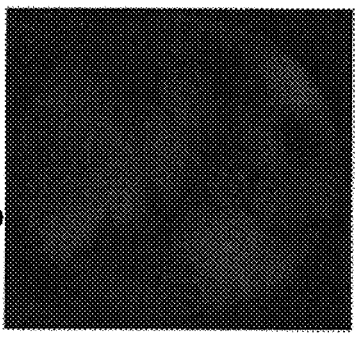
Figure 1D:
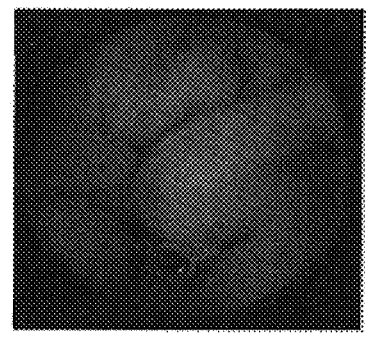
Figure 2A:
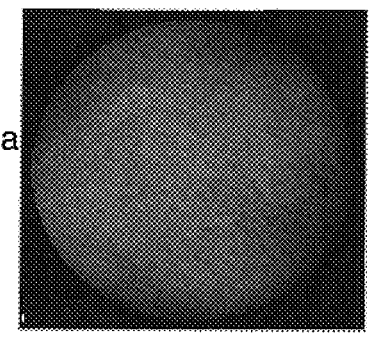
Figure 2C:
Figure 2B:
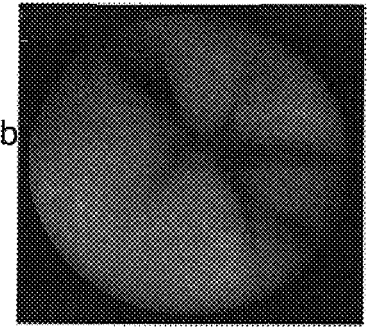
Figure 2D:
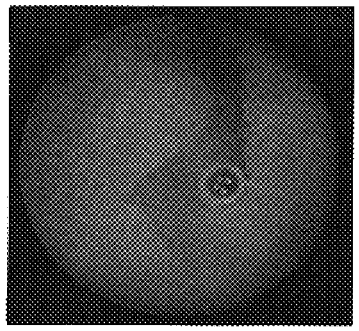
Figure 3A:
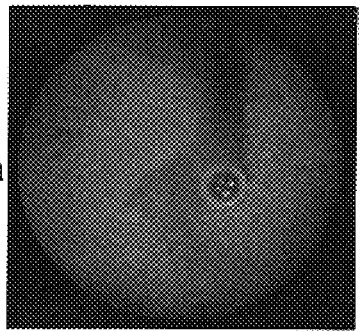
Figure 3B:
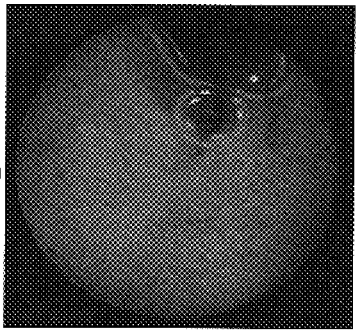
Figure 3C:
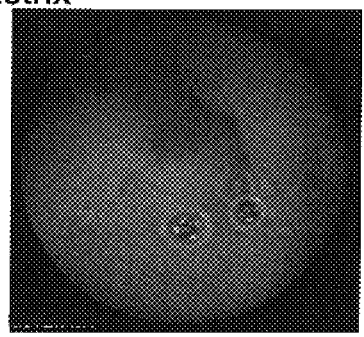
Figure 3D:
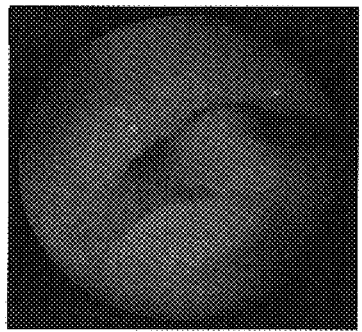
Figure 4A:
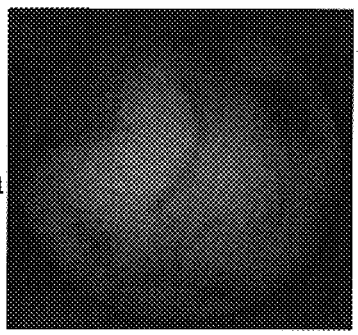
Figure 4C:
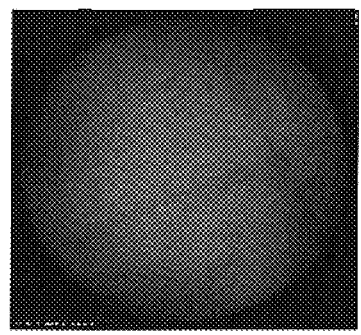
Figure 4B:
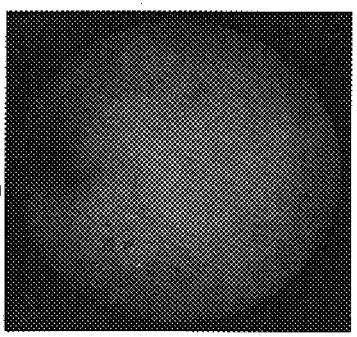
Figure 4D:
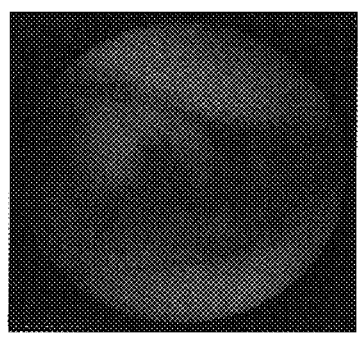

FIGS. 1*a*–*d* present capsule endoscopy images of a patient suffering from idiopathic inflammation of the small bowel (suspected as Crohn's disease), following treatment with the probiotic composition of the present invention, at a regimen of one tablespoon twice a day, following 2 weeks of treatment;

FIGS. 2*a*–*d* present capsule endoscopy images of the patient suffering from idiopathic inflammation of the small bowel (suspected as Crohn's disease), described in FIGS. 1*a*–*d*, following a second treatment with the probiotic composition of the present invention, at a regimen of one tablespoon twice a day following one month of treatment;

FIGS. 3*a*–*d* present capsule endoscopy images of a patient suffering from idiopathic inflammation of the proximal small bowel (IBD-related diarrhea); and FIGS. 4*a*–*d* present capsule endoscopy images of a patient suffering from idiopathic inflammation of the proximal small bowel (IBD-related diarrhea), described in FIGS. 3*a*–*d*, following treatment with the probiotic composition of the present invention, at a regimen of one tablespoon twice a day, following 2 weeks of treatment and thereafter with four tablespoons a day, following 4 weeks of treatment.

DESCRIPTION OF THE PREFERRED EMBODIMENTS

The present invention is of a pharmaceutical composition that comprises a non-pathogenic probiotic microorganism and the use thereof in the treatment of IBD such as Crohn's disease (distal and proximal), ulcerative colitis, indeterminate colitis, microscopic colitis, collagenous colitis, idiopathic inflammation of the small and proximal intestine and IBD-related diarrhea.

The principles and operation of the pharmaceutical composition and the method according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The present invention is based on the surprising findings that non-pathogenic strains derived from *E. coli* have a beneficial therapeutic activity in treating IBD. More specifically, the present invention is based on experimental results that show the superior activity of the probiotic *Escherichia coli* strain BU-230-98, ATCC Deposit No. 202226 (DSM 12799), deposited at American Type Culture Collection, 10801 University Boulevard, Manassas, Va. 20110-2209, USA, which is a derivative of the commercially available *Escherichia coli* strain M-17, which can be obtained, for example, from Biomed Ltd, Moscow, Russia; from BioPharma, 9 M. Amosova Vul., 03038 Kyiv (Kiev), Ukraine; or from Imbio, 44, Gruzinskava str., 603950, Nizhny Novgorod, Russia under the commercial name Colibacterium siccum, when administered to patients suffering from various idiopathic IBDs.

Hence, according to one aspect of the present invention, there is provided a method of treating or preventing an inflammatory bowel disease (IBD). The method is effected by administering to a subject in need thereof a therapeutically effective amount of at least one probiotic *E. Coli* strain.

Without being bound by any theory in particular, the therapeutic and prophylactic activity of the probiotic *E. Coli* strains with respect to IBDs, according to the present invention, presumably, stems from the fact that such strains, by efficiently altering the bacterial balance in the GI tract so as to normalize the function of the GI tract, further affect gastrointestinal inflammatory activity such as inflammatory bowel disease.

Preferred probiotic *E. Coli* strains for use according to the teachings of present invention include non-pathogenic *E. Coli* strains which exert probiotic activity. The presently most preferred probiotic *E. Coli* strain is the probiotic *Escherichia coli* strain BU-230-98, ATCC Deposit No. 202226 (DSM 12799), which is an isolate of the known, commercially available, probiotic *Escherichia coli* strain M-17. Recent studies (see, for example, U.S. patent application Ser. No. 09/725,846 and PCT/IL01/01088, which are incorporated herein by reference) have revealed that while *Escherichia coli* strain BU-230-98, ATCC Deposit No.

202226 (DSM 12799) is at least as efficacious as M-17 and is even superior thereto in probiotic applications, it is further advantageous over M-17, as it far better survives refrigerated storage in a liquid formulation. Nevertheless, the M-17 strain can also serve as a probiotic strain while implementing the present invention.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein, the term "treating" includes abrogating, substantially inhibiting, slowing or reversing the progression of a disease, substantially ameliorating clinical symptoms of a disease or substantially preventing the appearance of clinical symptoms of a disease.

The term "preventing" refers to barring a subject from acquiring a disorder or disease in the first place.

As used herein, the phrase "inflammatory bowel disease (IBD)" refers to a disorder or disease characterized by inflammatory activity in the GI tract. Examples of IBDs that are treatable by the probiotic strains of the invention include, without limitation, Crohn's disease (both distal and proximal), ulcerative colitis, indeterminate colitis, microscopic colitis, collagenous colitis, idiopathic inflammation of the small and/or proximal intestine and IBD-related diarrhea.

IBDs that are efficiently treatable by the method of the present invention include IBDs that involve inflammation of the small and/or proximal intestine. This inflammation can be either idiopathic or resulting from distal or proximal Crohn's disease.

The term "administering", as used herein, refers to a method for bringing the probiotic E. Coli strains into an area or a site in the GI tract that is affected by the IBD.

The term "therapeutically effective amount" refers to that amount of a probiotic E. Coli strain being administered, which will relieve to at least some extent one or more of the symptoms of the IBD being treated.

A therapeutically effective amount, according to the method of the present invention, preferably ranges between about $10^7$ and about $10^{12}$ viable bacteria per administration, more preferably between about $10^8$ and about $10^{11}$ viable bacteria per administration, more preferably between about $10^9$ and about $10^{11}$ viable bacteria per administration and most preferably it is between about $5 \times 10^9$ and about $2 \times 10^{10}$ viable bacteria per administration.

The term "about", as used herein, refers to ±10%.

The number of administrations according to the present invention preferably ranges between 1 and 10 administrations per day, more preferably between 1 and 5 administrations per day and most preferably between 2 and 4 administrations per day. The overall amount of viable bacteria that is administered daily, preferably ranges between $10^9$ and $10^{11}$ viable bacteria per day.

The probiotic strain of the present invention is preferably formulated and administered as a liquid formulation, as is described in detail hereinbelow and is further exemplified in the Examples section that follows.

The formulation of the probiotic strains of the present invention in a liquid formulation is highly advantageous. Being under biologically active conditions, the formulation serves also as a supportive medium for living bacteria, as opposed to lyophilized formulations, such as the commercial M17 preparation, where the bacteria are under anabiotic conditions. As a result, the liquid formulation of the invention, for example, is therapeutically active immediately following oral administration, as no biomass generation in the gut is required.

The liquid formulation of the probiotic E. Coli strain, according to the present invention, typically comprises a suspension of the bacteria in an aqueous solution. The aqueous solution is typically mainly comprised of distilled water, salt in an isotonic amount and can further comprise other ingredients, as is further detailed hereinbelow.

The liquid formulation of the probiotic E. Coli strain, according to the present invention, typically comprises between about $10^7$ and about $10^{10}$ CFU (colony forming units) of the probiotic Escherichia coli strain, per ml. Preferably, the liquid formulation comprises between about $10^7$ and about $10^9$ CFU per ml, more preferably between about $10^8$ and about $10^9$ CFU per ml and most preferably the liquid formulation comprises about $10^9$ CFU per ml.

According to a preferred embodiment of the present invention, between 10 ml and 20 ml per day of the liquid formulation is administered to a subject, between 2 and 4 times a day. Hence, as stated above, a daily dose, according to the present invention, preferably ranges between about $10^8$ and about $10^{11}$ viable bacteria, more preferably between about $10^9$ and about $10^{11}$ viable bacteria, more preferably between about $10^{10}$ and about $10^{11}$ viable bacteria and most preferably between $10^{10}$ and $2 \times 10^{10}$ viable bacteria.

The liquid formulation used in context of the present invention is orally administered and as such, it preferably further comprises one or more flavoring agent(s).

The flavoring agent can be any known Food grade additive, such as, for example, chocolate fudge flavor (available from Noville Essential Oil Col., North Bergen, N.J. 07047) and Base Strawberry (Cat. No. 10333-33,v Givaudan Dubendorf Ltd., Dubendorf, Switzerland CH-8600), and any other flavoring agents approved by the Fragrance Institute or any other regulatory authority. The flavoring agent can optionally be a sweetener such as, but not limited to, sucrose, corn syrup, saccharin and aspartame.

A representative example of a liquid formulation of a probiotic E. Coli strain includes a suspension of the bacteria in a distilled-water solution that comprises 0.6% sodium chloride and 0.1% flavoring agent such as Base Strawberry. It will be appreciated that the sodium chloride is primarily used for maintaining the liquid in the formulation isotonic to the bacteria cells and hence can be replaced by isotonically equivalent amounts of other highly water soluble salts.

Alternatively, the liquid formulation of the present invention comprises one or more volatile fraction(s) of a plant extract, as well as salts. A preferred volatile fraction, according to the present invention, is prepared by grinding a plant derived material to give a plant biomass; mixing the plant biomass with water and stirring at ambient temperature; steam distilling the plant extract at a pressure lower than atmospheric pressure and at a temperature that does not exceed 38° C.; and collecting the volatile fraction obtained from the steam distillation. Preferably, the pressure is of 5–10 mbar. A detailed description of such volatile fractions and the preparation thereof is found, for example, in U.S. Pat. No. 6,500,423, which is incorporated herein by reference. The plant matter from which the volatile fraction may be obtained may be any suitable plant part, such as fruit, leaf, stem or root. Many plants are suitable as a source for the volatile fractions, for example apple, citrus, soy bean, beet, cabbage, garlic and alfalfa, as well as herbs such as parsley, mint and dill.

The use of volatile fractions of plant extracts prepared as described hereinabove within the liquid formulation of the present invention is particularly advantageous as these volatile fractions are known to maintain the viability of microorganisms for a prolonged period of time, at room temperature and/or when refrigerated. Hence, liquid formulations that comprise a probiotic *E. Coli* strain and a volatile fraction of a plant extract can be stored for long time periods under standard conditions and therefore have a long shelf-life. The volatile fractions can further serve as flavoring agents. In addition, it is shown in PCT/IL01/01088 that the volatile fractions described herein have therapeutic activity in themselves with respect to GI disorders.

The liquid formulations of the present invention can further comprise a beehive product such as honey, propolis and any other apicultural product.

Treating an IBD with a probiotic *E. Coli* strain is highly advantageous as compared to the presently known methods as it provides for an effective, side effects-free, non-invasive treatment and it further provides for facile and effective route of administration as the probiotic bacteria is formulated and administered orally, preferably as a liquid formulation.

According to another aspect of the present invention there is provided a pharmaceutical composition that comprises, as an active ingredient, the probiotic *E. Coli* strain described hereinabove. The pharmaceutical composition of the present invention is identified for use in the treatment or prevention of an IBD, as is defined hereinabove.

As used herein a "pharmaceutical composition" refers to a preparation of the probiotic *E. Coli* strains described herein, with other chemical components such as pharmaceutically suitable carriers and excipients. The purpose of a pharmaceutical composition is to facilitate administration of an active ingredient to a subject.

Hereinafter, the term "pharmaceutically acceptable carrier" refers to a carrier or a diluent that does not cause significant irritation to a subject and does not abrogate the biological activity and properties of the administered active ingredient.

Herein the term "excipient" refers to an inert substance added to a pharmaceutical composition to further facilitate administration of the active ingredient.

The pharmaceutical composition of the present invention is preferably a liquid formulation, as is described in detail hereinabove, however lyophilized formulations can also be used.

According to a preferred embodiment of the present invention, the carrier is an aqueous solution in which the bacteria are suspended. The aqueous solution can be, for example, saline that comprises a volatile fraction of a plant extract and/or flavoring agent(s).

Techniques for formulation and administration of drugs may be found in "Remington's Pharmaceutical Sciences," Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the active ingredients into preparations which can be used pharmaceutically.

For oral administration, the *E. Coli* strains can be formulated readily by combining the *E. Coli* strains with pharmaceutically acceptable carriers as described herein. Such carriers enable the *E. Coli* strains of the invention to be formulated as tablets, pills, dragees, capsules, liquids, gels, syrups, slurries, suspensions, and the like, for oral ingestion by a patient. Alternatively, the *E. Coli* strains may be in powder form for constitution with a suitable vehicle, e.g., sterile, pyrogen-free water or saline, before use.

The amount of a composition to be administered will, of course, be dependent on the subject being treated, the severity of the affliction, the manner of administration, the judgment of the prescribing physician, etc.

The pharmaceutical compositions of the present invention are presented in a packaging material, such as a FDA approved kit, which may contain one or more unit dosage forms containing the active ingredient. The packaging material may, for example, comprise metal or plastic foil, such as a blister pack. The pharmaceutical compositions are identified in print, on or in the packaging material, for use in the treatment or prevention of an IBD, as is defined hereinabove. The packaging material may be accompanied by instructions for administration. The packaging material may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Preparation of the Probiotic Composition for Treating IBD

A representative probiotic composition for treating IBD according to the present invention includes the following components:

*Escherichia coli* strain BU-230-98 ATCC Deposit No. 202226 (DSM 12799), also referred to herein as *E. coli* ATCC 202226, between $10^7$ CFU per ml and $10^9$ CFU per ml;

Sodium chloride, about 0.6%; and

Base Strawberry, about 0.1% in distilled water.

One hundred bottles, each containing 250 ml of the probiotic preparation described above, were prepared as follows:

All the operations were performed in a sterile room or in a laminar hood.

E. Coli cells were grown in four 2 liters Erlenmeyer flasks, each containing 500 ml of a medium consisted of: 10 grams/liter Bacto Soytone (DIFCO), 5 grams/liter Yeast extract (DIFCO), 2 grams/liter Glucose, and 10 grams/liter NaCl, at pH=7.0. The medium was inoculated at about 0.1% of the final $OD_{650}$ either from slants or directly from a suspension in glycerol preserved at −80° C.

The flasks were placed in a New Brunswick Rotatory shaker rotating at 250 rpm, for 18 hours, at 30° C. The growth resulted in 2 liters of fermentation broth containing, at the pH=7.3, cell suspension of $OD_{650}$=6.8.

The cells were harvested by centrifugation for 10 minutes at 10,000×g, in sterile centrifugation bottles, and thoroughly washed with a 0.6% sodium chloride solution in water, so as to remove the traces of the fermentation broth. The washed cell precipitate was re-suspended in 26 liters of a steam-sterilized solution that included 0.6% NaCl and the Food grade flavor additive Base Strawberry (Cat. No. 10333-33,v Givaudan Dubendorf Ltd., Dubendorf, Switzerland CH-8600). The obtained stock solution of Base Strawberry in steam-sterilized 0.6% NaCl (50 grams/liter) was filtered through 0.2 μm filter (Corning). The resulting microorganisms' suspension had the $OD_{650}$=0.48 and contained about $10^9$ CFU/ml. The composition was then transferred into sterile plastic culture bottles in portions of 250 ml.

Example 2

Treatment of Crohn's Disease Using E. coli (ATCC 202226)

A 34-year-old male suffering for five months from irregular bowel habits, tenesmus, frequent defacations with passage of mucus and no significant weight loss was studied for the efficacy of E. coli (ATCC 202226) as a therapeutic agent of IBD, as compared to other known IBD drugs. The family history of the patient indicates that his father and three of his siblings suffer from Crohn's disease.

Laboratory tests of the patient revealed the following: Hemoglobin=17, ESR=4, platelet count of 214, negative serological markers for Celiac disease, negative stool cultures and direct exam, albumin=4.2.

In a colonoscopy performed by inserting the colonoscope into the distal ileum it was found that the mucosa of the small bowel appeared granular. A biopsy of that area documented some loss of glands. The findings of the colon were normal and a random biopsy of the rectum was normal too.

The patient was treated with 3 grams of 5-amino-salicylic acid (5-ASA). Following this treatment the patient had reported an improvement in his condition, although he still complained of having abdominal cramps and diarrhea. Raising the dose of 5-ASA to 4 grams per day resulted in no further improvement. The patient was treated with 5-ASA as well as with antispasmodics during a period of more than a year, with no substantial improvement in his medical condition.

Following this unsuccessful treatment, a probiotic composition which comprised E. coli (ATCC 202226) prepared as described hereinabove, was administered to the patient, at a regimen that included a tablespoon twice a day, approximately half an hour before meals. After 2 weeks, the patient reported that his symptoms significantly improved.

Then, the probiotic treatment was ceased. Since the symptoms and complaints were restored following the cessation, a capsule endoscopy was performed in order to further study objective parameters in reference to his complaints and to the effectiveness of the probiotic composition.

As is shown in FIGS. 1a–d, the capsule endoscopy study revealed prominent inflammatory changes in the proximal small bowel including erosions, mucosal hemorrhages, edema and areas with loss of villi. During this cessation of the probiotic treatment, the patient's bothersome abdominal complaints returned.

The probiotic treatment was then reinstated. After one month, a second capsule endoscopy study was performed. As is shown in FIGS. 2a–d, the capsule endoscopy study revealed significant improvement of the inflammatory changes of the proximal small bowel.

Example 3

Treatment of IBD-Related Diarrhea Using E. coli (ATCC 202226)

A 23-year-old male, suffering from loose bowel movements with episodes of diarrhea for two years, and having no rectal bleeding or weight loss, was studied. His family history was unremarkable for bowel disease.

Laboratory tests of the patient showed the following: Hemoglobin=17.6 (smoker), ESR=10, Platelets=219, Albumin=4.1, tissue transglutaminase TTG=29.8 (normal <20).

In addition, the patient was found to have lactose intolerance by a positive H2 breath test. However, a diet free of dairy products did not improve his condition.

The patient's elevated TTG value suggested a diagnosis of Celiac disease. An upper GI endoscopy revealed a normal appearing small bowel. A random biopsy from the second part of the duodenum documented the presence of normal small bowel mucosa. A capsule endoscopy study was preformed and, as is shown in FIGS. 3a–d, revealed inflammatory changes in the proximal small bowel including a few erosions, mucosal hemorrhages, edema and loss of villi.

The patient was treated with a probiotic composition prepared as described in Example 1 at a regimen of one tablespoon twice daily, approximately half an hour before meals. After 2 weeks there was no improvement in the patient's condition. The probiotic treatment of the patient was continued while raising the daily dose to four tablespoons daily. Following this treatment, the patient reported substantial improvement, for the first time in two years. A second capsule endoscopy of the small bowel demonstrated improvement of the inflammatory process of the proximal small bowel, as is shown in FIGS. 4a–d.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating an inflammatory bowel disease (IBD) selected from the group consisting of Crohn's disease and IBD-related diarrhea in a subject suffering from said inflammatory bowel disease, the method comprising administering to the subject a therapeutically effective amount of the probiotic *Escherichia coil* strain BU-230-98 (ATCC Deposit No. 202226 DSM 12799).

2. The method of claim 1, wherein said probiotic *Escherichia coli* strain is administered to the subject in a liquid formulation.

3. The method of claim 1, wherein said probiotic *Escherichia coli* strain is administered to the subject orally.

4. The method of claim 2, wherein said liquid formulation comprises between $10^7$ and $10^{10}$ CFU per ml of said probiotic *Escherichia coli* strain.

5. The method of claim 2, wherein said liquid formulation comprises at least one volatile fraction of a plant extract.

6. The method of claim 2, wherein said liquid formulation comprises at least one flavoring agent.

7. The method of claim 6, wherein said at least one flavoring agent is Base Strawberry.

8. The method of claim 5, wherein said volatile fraction is prepared by water extraction of said plant followed by steam distillation under a pressure lower than atmospheric pressure and at a temperature not exceeding 38° C.

9. The method of claim 5, wherein said liquid formulation further comprises a beehive product.

10. The method of claim 9, wherein said beehive product is propolis.

11. The method of claim 6, wherein said liquid formulation further comprises a beehive product.

12. The method of claim 11, wherein said beehive product is propolis.

13. The method of claim 1, wherein said inflammatory bowel disease is Crohn's disease.

14. The method of claim 1, wherein said inflammatory bowel disease is IBD-related diarrhea.

15. The method of claim 1, wherein said therapeutically effective amount is between about $10^7$ and about $10^{12}$ viable bacteria per administration, ranging from 1 to 10 administrations per day.

* * * * *